United States Patent [19]

Brunke et al.

[11] Patent Number: 4,490,284

[45] Date of Patent: Dec. 25, 1984

[54] 1,1-DI($C_1$-$C_6$-ALKYL)-2-PHENYL-ETHANE DERIVATIVES AS PERFUMING INGREDIENTS

[75] Inventors: Ernst-Joachim Brunke; Erich Klein, both of Holzminden, Fed. Rep. of Germany

[73] Assignee: Dragoco Gerberding & Co. GmbH, Holzminden, Fed. Rep. of Germany

[21] Appl. No.: 427,989

[22] Filed: Sep. 29, 1982

[51] Int. Cl.³ .............................................. A61K 7/46
[52] U.S. Cl. .................. 252/522 R; 426/534; 424/50; 424/365
[58] Field of Search .................. 252/522 D, 522 R; 424/50, 36 T; 426/534

[56] References Cited

FOREIGN PATENT DOCUMENTS 3139358 4/1983 Fed. Rep. of Germany .

OTHER PUBLICATIONS

Diet et al., "Tet. Letters", (1973), No. 15, pp. 1273-1275.
Arctander, "Perfume & Flavor Chemicals", II, (1969), Nos. 2541, 2586, 2589 and 2580.

Primary Examiner—Anton H. Sutto
Attorney, Agent, or Firm—Anthony J. Casella; Gerald E. Hespos

[57] ABSTRACT

A process for imparting, enhancing or modifying the flowery odorous note in perfumes, perfume compositions or artificial essential oils, for use in a perfume composition, a perfumed article, a cologne, a foodstuff, an alcoholic or nonalcoholic beverage, a toothpaste, a medicinal product or a chewing gum, comprising the step of adding an organoleptic property modifying quantity of 1,1-Di($C_1$-$C_6$-alkyl)-2-phenylethan derivatives of formula A, wherein R is a formyl-, hydroxymethyl-, formoxymethyl-, acetoxymethyl- or a nitrilo group and the total number of carbon atoms in both alkyl substituents together is at most 8.

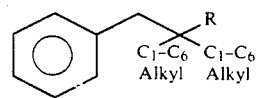

a: R = CHO    A
b: R = $CH_2OH$
c: R = $CH_2Ac$
d: R = CN
e: R = $CH_2OCHO$

19 Claims, No Drawings

1,1-DI(C$_1$-C$_6$-ALKYL)-2-PHENYL-ETHANE DERIVATIVES AS PERFUMING INGREDIENTS

THE INVENTION

The present invention relates to the field of perfumery and flavoring, in particular it relates to the use of 1,1-dialkyl-2-phenyl-ethan-derivative Ae–e, wherein R is a formyl-, hydroxy-, methyl-, acetoxymethyl-, nitrilo- or formoxymethyl group, as an aroma chemical or as a constituent of fragrance compositions in particular for cosmetic and technical perfumes.

The invention will first be described on the basis of the α,α-dimethyl-derivatives 1a–1d.

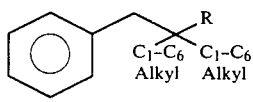

a: R = CHO
b: R = CH$_2$OH
c: R = CH$_2$Ac
d: R = CN
e: R = CH$_2$OCHO

A

BACKGROUND OF THE INVENTION

Aroma chemicals with floral olfactory characteristics are of great interest to the perfume industry. Since the distillates or extracts of plants containing the appropriate characteristic fragrance are either very expensive—as is the case with attar of roses or jasmine-absolue-, or un-obtainable because of their instability- for example lilac or lily of the valley-, it has always been the aim of the aroma chemical industry to prepare synthetic substitute products. Whereas chemical partial or total synthesis already exist for most of the different active perfuming ingredients in stable plant distillates or extracts, and these are often suitable for manufacture, only technically stable, synthetic substitutes are available for the unstable natural fragrances such as lily of the valley or lilac, which may have a similar fragrance to the natural product but have a different structure. Examples of this kind of widely used sythetic aroma chemicals with floral olfactory characteristics include dimethyl-benzyl-carbinol (2) or phenylethyldimethyl-carbinol (3). The odour of compound 2 is described as warm, herbal-floral, slightly animal with a side note of freshly cut wood and nuances of lily and elder flower (S. Arctander, Perfume and Flavor Chemicals, 1969, Nr 989) Compound 3 (Arctander, Nr. 1043) has a floral, green slightly herbal and oily odour reminiscant of lily and hyacinth. Both compounds 2, 3 are only obtainable by means of Grignard-reactions, which require relatively sophisticated technology.

The secondary alcohols anologous to the tertiary alcohols 2 and 3 are not used in perfumes, however the corresponding primary alcohols 4 and 5 are. However the odour notes of these compounds are very different from those of 2, 3.

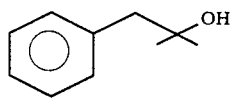

2

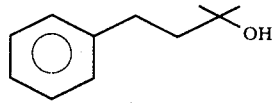

3

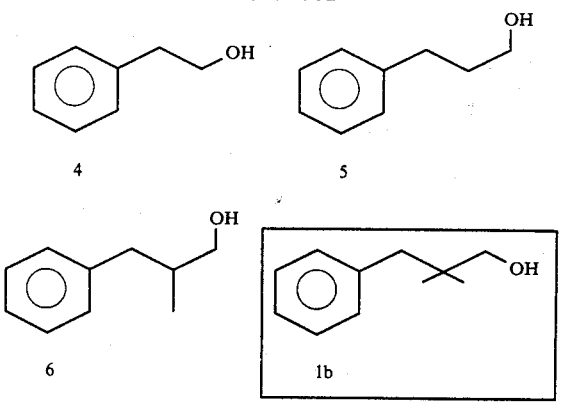

The odour of phenylethyl-alcohol (4), which is used in large amounts, is described as "mild and warm, rose- and honey-like" (Arctander, Nr. 2513). Dihydrocinnamic-alcohol (5) has an odour resembling cinnamon, described as "warm and mild, balsamic- floral, sweet" (Arctander, Nr. 2589). α-methyl-dihydro-cinnamic alcohol (6) prepared by means of aldol condensation of benzaldehyde and propionaldehyde with subsequent hydrogenation has a very week, cinnamon like-sweet, slightly woody odour and is not used as an aroma chemical.

PREFERRED EMBODIMENTS OF THE INVENTION

It is therefore suprising that α,α-dimethyl-substituted primary alcohol 1b has a strong diffusive and pleasantly floral odour resembling lily of the valley and hyacinth, reminiscant of certain olfactory aspects of tertiary carbinols, but having a superior natural character in perfume compositions. α,α-dimethyl-compound 1b has been described in chemical literature, but its particular olfactory characteristics were neither recognized nor mentioned. [V. G. Purohit and R. Subramanian, Chem. and Ind. 1978, 731. P. Warrick and W. H. Saunders, J.Am. Chem. Soc., 84, 4095 (1962); A. Haller and E. Bauer, Ann. Chim., 9, 15 (1918)]. It was discovered that the olfactory characteristics of compound 1b make it very suitable for incorporation in fragrances of a floral type, giving these a more natural character.

Aldehyde 1a has a pronounced aldehydic-green odour which is suitable for in-corporation in fragrances, especially in low dosages. The preparation of α,αdimethyl-substituted aldehyde 1a has been described by H. K. Dietl and K. C. Brannock (Tetrahedron Letters 1973, 1273), but the olfactory characteristics of the compound were not mentioned.

We prepared various esters from primary alcohol 1b using the usual esterification process. Of these the acetate 1c and the formiate 1b have particular olfactory effects. The odour notes of 1c may be described as "woody, sweet-herbal, floral" and those of 1e, as "woody, herbal, green". The nitrile 1d has a herbal-balsamic odour with floral and fruity side-notes. Compounds 1a–1d may be prepared from basic chemicals in a relatively simple manner and can therefore be produced in large amounts.

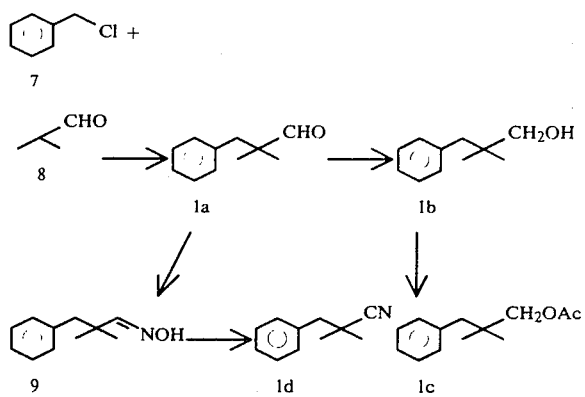

Substances 1a–d are prepared from benzylchloride (7), which has been converted to aldehyde 1a in a known per se manner in a phase-transfer reaction with isobutyraldehyde (8). This reaction has been described, using 50% aqueous sodium hydroxide and catalytic amounts of tetrabutyl-ammonium-iodide as catalyst (H. K. Dietl and K. C. Brannock, Tetrahedron Letters 1973, 1273). It was discoverd that the expensive tetrabutylammonium-iodide used by Dietl and Brannock could be replaced by cheaper tricapryl-methyl-ammonium-chloride (Aliquat 336). The reaction is carried out at high temperature, preferably at boiling point, in a two-phase system consisting of toluene and a 50% solution of NaOH. Approximately 60% yield of aldehyde 1a was obtained by means of the usual processing and distillation. The reduction of aldehyde 1a to the primary alcohol 1b is preferably carried out by means of catalytic hydrogenation using Raney-Nickel or copper-chromite in undiluted condition or using polar aprotic solvents such as methanol. The reduction was also carried out using hydrides such as sodiumborohydride or lithiumaluminiumhydride, observing the usual conditions for the reaction.

Esterification was carried out in a known per se manner by converting the alcohol 1b with acid anhydrides in the presence of acid binding substances such as sodium carbonate or potassium carbonate. The acetate 1c was prepared by converting 1b with acetanhydride/sodiumcarbonate.

The nitrile 1d was prepared in a known per se manner by reacting hydroxylamine with 1a in a basic medium producing oxime 9 which was subsequently dehydrated by the action of acetanhydride at boiling point.

The reaction steps described for the preparation of compounds 1a–1d are transferable to homologous compounds. Thus α-alkyl-substituted aldehyde with a maximum of 10 carbon atoms, such as 2-methyl-butanal, 2-methyl-pentanal, 2-ethyl-butanal, 2-ethyl-pentanal, 2-ethyl-hexanal, 2-propylpentanal may be alkylated with benzylchloride using phase transfer catalysts, preferably tricaprylammoniumchloride and alkalimetalhydroxides. The aldehydes with the general formula Aa produced in this way have fresh notes and some have woody-herbal notes. The acetates with the general formula Ac prepared in an analogous fashion to 1c have woody and sweet-herbal odour notes, whereas the primary alcohols with the general formula Ab obtained in an anologous fashion to 1d have mild-floral, sometimes fresh olfactory aspects. The nitriles with the general formula. Ad obtained in analogous fashion to 1d have sweet-floral and herbal notes, and the formiates Ae have fresh-woody notes.

The olfactory aspects of compounds Aa–d become heavier and less bright as their molecular weight increases, sometimes also less intense than the dimethyl-substituted compounds 1a–d. On the other hand, the fixative and rounding effects in perfume compositions are more dominant at higher molecular weights. On the basis of their olfactory characteristics, their fixative characteristics and their stability in cosmetic and technical media, the compounds with the general formuli Aa–Ae are very suitable for perfuming cosmetic and technical products.

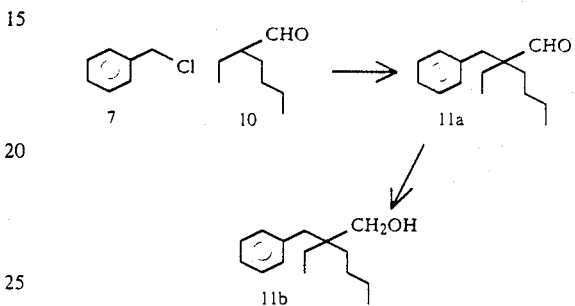

The aldehyde 11a with 15 carbon atoms corresponding to the general formula Aa was prepared from benzylchloride (7) and α-ethyl-hexanal (10) according to the method given for 1a. The odour notes may be described as bright, herbal, fruity (Agrumen-aspects). Alcohol 11b with mild-floral notes was obtained by means of reduction in an analogous fashion to 1b.

The following examples describe the preparation of compounds 1a–d and their application in fragrances.

EXAMPLE 1

Preparation of 2,2-dimethyl-3-phenyl-propanal-1 (1a):

While being stirred, 200 ml toluol was added to a solution of 224 g (4 mol) KOH and 10 g tricapryl-methyl-ammonium-chloride (Aliquat 336) in 125 g water and brought to boiling point. As boiling continued, a solution of 402 g (3.2 mol) benzylchloride (7) and 256 g (3.6 mol) isobutyraldehyde was added drop by drop over 1 hour. After the mixture had been stirred for 7 hours at boiling point and cooled to room temperature, it was diluted with 300 g water. The aqueous phase was extracted with toluene The united organic phases were neutralized and concentrated. The raw product (510 g yellow oil) was distilled on a 60 cm packed glass column and produced 354 g (69%) 1a in the form of a colourless oil.bp. (2 mm)=73° C. —NMR (CCl$_4$): δ=0.92, s, 6H (2,2—CH$_3$), 7.0–7.4, m (phenyl—H), 9.65 ppm, s (CH—1). —IR: 1730, 2740 cm$^{-1}$ (aldehyde). —MS: m/e (%)=162 (20, M$^+$), 147 (4), 133 (7), 115 (5), 105 (4), 91 (100). C$_{11}$H$_{14}$O (162.2).

EXAMPLE 2

Preparation of 2,2-dimethyl-3-phenyl-propanol (1b):

354 g 2,2-dimethyl-3-phenyl-propanal (1a) was hydrogenated in an autoclave with 2 g copper chromite (G-79) at 150° C. and 120 bar until it had absorbed 1 equivalent of hydrogen. When the pressure had been released in the autoclave the catalyst was separated off. Distillation on a 60 cm packed column yielded 320 g (90%) 2,2-dimethyl-3-phenyl-propanal (1b) in the form of a colourless, viscous oil. bp (2 mm)=90° C., mp. 34°-36° C. —NMR (CCl$_4$): δ−0.88, s, 6H (2,2—CH$_3$), 2.55, s (CH$_2$—3), 3.37, s (CH$_2$—1), 7.1-7.3, br.s (phenyl—H). —IR: 3400 cm$^{-1}$ (O—H). —MS: m/e (%)=164 (16, M$^+$), 133 (5), 131 (4), 117 (6), 115 (8), 105 (4), 92 (100), 91 (83). C$_{11}$H$_{16}$O (164.2).

EXAMPLE 3

Preparation of 2,2-dimethyl-3-phenyl-propyl-1-acetate (1c):

A solution of 100 g 2,2-dimethyl-3-phenyl-propan-1-ol (1b) and 20 g sodium acetate was heated at boiling point for 3 hours in 100 g acetic anhydride. Following the usual process the raw product (105 g straw-coloured oil) was distilled on a 30 cm packed glass column. 90 g 1c was obtained in the form of a colourless oil. bp (2 mm) 0 90° C. —NMR (CCl$_4$): δ=0.87, s, 6H (2,2—CH$_3$), 1.98, s (—O—CO—CH$_3$), 2.53, s (CH$_2$—3), 3.73, s (CH$_2$—1), 6.9-72 ppm, m (phenyl—H). —IR: 1735 cm$^{-1}$ (acetate).—(35), 43 (100). C$_{13}$H$_{18}$O$_2$ (206.3).

EXAMPLE 4

Preparation of 2,2-dimethyl-3-phenyl-propionitrile (1d):

At 20°-30° C., while being stirred, 36 g aqueous sodiumhydroxide (33%) was added to a solution of 22.7 g (0.25 mol) hydroxyl-aminehydrogensulfate in 40 ml methanol and 20 ml water. Subsequently 40.5 g (0.25 mol) 2,2-dimethyl-3-phenyl-propanal (1a) was run in and the reaction mixture was stirred for 3 hours at room temperature. By way of further processing it was diluted with 150 ml water and extracted with methylenchloride. After concentration there remained ca. 45 g oxime 9, which was added to 80 g boiling acetic anhydride over 20 minutes. After 5 hours stirring at boiling point, it was diluted with 200 ml water, extracted with benzine and concentrated. The raw product (6.40 g) was distilled on a short column and subsequently cristallized from ethanol, producing 20 g 1d with a melting point of 55°-56° C. —NMR (CCl$_4$): δ=1.27, s, 6H (2,2—CH$_3$), 2.71, s (CH$_2$—3), 7.1-7.3 ppm (phenyl—H). —IR: 2230 cm$^{-1}$ (nitrilo). —MS: m/e (%)=159 (11, M$^+$), 146 (3), 132 (3), 117 (6), 115 (3), 91 (100), 65 (9). C$_{11}$H$_{13}$N (159.2).

EXAMPLE 5

| Perfume oil with lily of the valley note | a | b |
|---|---|---|
| 1-formyl-4-(4-methyl-4-hydroxy-amyl)-cyclohexene-3 [Lyral ®] | 190 | 190 |
| α-hexyl cinnamicaldehyde | 170 | 170 |
| citronellol | 145 | 145 |
| phenyl ethyl dimethyl carbinol (3) | 130 | — |
| 2,2-dimethyl-3-phenyl-propanol (1b) | — | 130 |
| 2-phenyl ethanol | 120 | 120 |
| lilial | 40 | 40 |
| indole, 10% in DPG | 35 | 35 |
| cyclopentadecanolide, 1% in DPG | 25 | 25 |
| 1-(3-hydroxy-hexyl)-2,2,6-trimethyl cyclohexane | 15 | 15 |
| cis-3-hexenol-1, 10% in DPG | 10 | 10 |
| cis-3-hexenyl-1-acetate, 10% in DPG | 10 | 10 |
| jasmine absolue, 10% in | 10 | 10 |
| | 900 | 900 |

DPG = Di propylen glycol

Perfume oil a has a balanced lily of the valley odour. Mixture b, in which alcohol 1b according to the invention is substituted for carbinol 3, also has a harmonious lily of the valley odour complex, which, however, is characterized by more body and natural diffusiveness as mixture a.

EXAMPLE 6

| Perfume oil with fougere note | a | b |
|---|---|---|
| Geraniol | 100 | 100 |
| Citronellol | 100 | 100 |
| Benzyl acetate | 90 | 90 |
| Phenyl ethyl alcohol | 80 | 80 |
| Patchouli oil, Singapore | 80 | 80 |
| α-amylcinnamicaldehyde | 75 | 75 |
| α-methyl-ionone | 45 | 45 |
| Amyl salicylate | 45 | 45 |
| Lavandin abrialis | 45 | 45 |
| Bergamot oil. Reggio | 45 | 45 |
| Terpineol | 40 | 40 |
| Coumarin | 30 | 30 |
| 1-(4-hydroxy-3-methyl-butyl)-2,2,3-trimethyl cyclopentene-2 (Brahmanol ®) | 30 | 30 |
| 1,3,4,6,7,8-hexyhydro-4,6,6,7,8,8-hexanethyl-cyclpenta-γ-2-benzopyrane (Galaxolide ®) | 25 | 25 |
| Benzoe-resinoid, Siam | 10 | 10 |
| Styrax extract | 10 | 10 |
| Oak moss extract | 10 | 10 |
| Dipropylene glycol | 130 | — |
| 2,2-dimethyl-3-phenyl-propyl-1-acetate (1c) | — | 130 |
| | 990 | 990 |

The fragrance mixture a has an odour complex of the Fougère-type with woody, dry-sweet aspects. Fragrance b, which additionally contains the new compound 1c, has an odour complex of the similar type, in which, however, a sweet-powdery note is emphasized and which also has a clearly rounded and more harmonious effect.

EXAMPLE 7

| Perfume oil "lilac" | a | b | c |
|---|---|---|---|
| Terpineol | 350 | 350 | 350 |
| 2,2-dimethyl-3-phenyl-propanol (1b) | — | 150 | — |
| Dipropylene glycol | 150 | — | 100 |
| Phenyl ethyl alcohol | 100 | 100 | 100 |
| 2,2-dimethyl-3-phenyl-propionitrile (1d) | — | — | 50 |
| Benzyl acetate | 50 | 50 | 50 |
| Lilial | 50 | 50 | 50 |
| Geraniol | 45 | 45 | 45 |
| Methyl-dihydrojasmonate | 40 | 40 | 40 |
| Linalool | 40 | 40 | 40 |
| Cinnamic alcohol | 20 | 20 | 20 |
| p-toyl acetaldehyde, 50% in DPG | 35 | 35 | 35 |
| Farnesol | 20 | 20 | 20 |
| Benzyl isoeugenol | 20 | 20 | 20 |
| Citronellol | 10 | 10 | 10 |
| Linalool oxide | 10 | 10 | 10 |
| Indol, 10% in DPG | 5 | 5 | 5 |
| cis-3-hexenol, 10% in DPG | 5 | 5 | 5 |
| Isojasmon | 3 | 3 | 3 |
| Isoeugenol | 2 | 2 | 2 |
| cis-3-hexenyl acetate, 10% in DPG | 2 | 2 | 2 |
| Eugenol methyl ether | 2 | 2 | 2 |
| p-kresol, 10% in DPG | 1 | 1 | 1 |
| | 960 | 960 | 960 |

Fragrance a has a balanced lilac odour. The fragrance obtained by replacing the odourless dipropylene-glycol with 15% carbinol 1b has a more diffusive lilac odour with a more natural effect. The addition of 5% nitrile 1d emphasizes the herbal-green aspects, producing an original floral-fresh odour complex.

EXAMPLE 8

| Perfume oil with powdery-sweet character | a | b | c |
|---|---|---|---|
| Bergamot oil | 350 | 350 | 350 |
| Amyl salicylate | 130 | 130 | 130 |
| Benzyl acetate | 100 | 100 | 100 |
| Anis aldehyde | 50 | 50 | 50 |
| Heliotropin | 50 | 50 | 50 |
| Benzoe-extract, Siam | 30 | 30 | 30 |
| Geranium oil, Bourbon | 30 | 30 | 30 |
| Musk, ambrette | 30 | 30 | 30 |
| Phenyl athyl alcohol | 30 | 30 | 30 |
| Coumarin | 20 | 20 | 20 |
| Nerol | 10 | 10 | 10 |
| Citronellol | 10 | 10 | 10 |
| Vanillin | 5 | 5 | 5 |
| Methyl chavicol | 5 | 5 | 5 |
| Oak moss extract, 50% in DPG | 4 | 4 | 4 |
| Citral | 2 | 2 | 2 |
| Isojasmon | 2 | 2 | 2 |
| Thymol, 10% in DPG | 1 | 1 | 1 |
| 3-methyl-5-propyl-cyclohexenon | 1 | 1 | 1 |
| Dipropylene glycol | 40 | — | — |
| 2,2-dimethyl-3-phenyl-propionitrile (1d) | — | 40 | — |
| 2,2-dimethyl-3-phenyl propanal (1a) | — | — | 40 |
|  | 900 | 900 | 900 |

The fragrance composition a has a classical sweet-powdery note with woody and spicy aspects. Mixture b, obtained by adding nitrile 1d according to the invention, has a more harmonious and softer effect, simultaneoulsy emphasizing sweet-spicy side notes. Addition of 5% of the aldehyde 1a (mixture c) according to the invention produces a new odour complex characterized by fresh diffusiveness with a woody-sweet top note and green-herbal side notes.

EXAMPLE 9

Preparation of 2-ethyl-2-benzyl-hexanal-1 (11a):

Using a method analogous to that in example 1, aldehyde 11a was obtained from benzylchloride (7) and α-ethyl-hexanal (10), producing a yield of 62% in the form of a colourless oil. bp (2 mm)=110° C. —NMR 8CCl$_4$): δ=0.84 t, 6H (—CH$_2$—CH$_3$), 2-75, s (∅—CH$_2$—), 7.0-7.2, m (aromat. H), 9.7 ppm (—CHO). —IR: 2750, 1725 cm$^{-1}$ (aldehyde). —MS: m/e (%)=218 (2, M+), 189 (6), 162 (7), 133 (4), 119 (5) 105 (7), 92 (18), 91 (100). C$_{15}$H$_{22}$O (218.3).

EXAMPLE 10

Preparation of 2-ethyl-2-benzyl-hexanol-1 (11b):

Using a method anologous to that in example 2, alcohol 11b was obtained from 11a, producing a yield of 90% in the form of a colourless oil with bp (2 mm)=125° C. NMR (CCl$_4$): δ=0.88, br. t, CH (—CH$_2$—CH$_3$), 2.58, s (∅—CH$_2$—), 3,25, s (—CH$_2$—OH), 7.13 ppm, s (aromat. H) —IR: 3400 cm$^{-1}$ (OH). —MS: m/e (%)=220 (4, M+), 128 12), 92 (100), 91 (62), 69 (47). C$_{15}$H$_{24}$O (220.3).

EXAMPLE 11

| Perfume oil with fresh Agrumen-note | |
|---|---|
| lemon oil | 250 |
| orange oil, Florida | 250 |
| Bergamott oil | 230 |
| Lavender oil | 50 |
| Neroli oil | 50 |
| Rosmarin oil, Tunesian | 30 |
| 2-ethyl-1-ethylendioxy-hexan | 20 |

| Perfume oil with fresh Agrumen-note (continued) | |
|---|---|
| Geraniol | 10 |
| α-hexyl-cinnamicaldehyde | 5 |
| Musk, Ketone | 5 |
|  | 900 |

This fragrance has a harmonious odour complex of the Agrumen-type with fresh green-herbal notes. After additon of 100 parts 2-benzyl-2-ethyl-hexanal (11a) the fragrance has a more delicate and natural effect. This also has an obvious fixative effect on the odour complex.

What we claim is:

1. A process for imparting, enhancing or modifying the flowery odorous note in perfumes, perfume compositions or artificial essential oils, for use in a perfume composition, a perfumed article, a cologne, a foodstuff, an alcoholic or nonalcoholic beverage, a toothpaste, a medicinal product or a chewing gum, comprising the step of adding an organoleptic property modifying quantity of a compound of the formula:

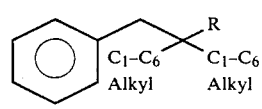

wherein R is a formyl-, hydroxymethyl-, formoxymethyl-, acetoxymethyl- group and the total number of carbon atoms in both alkyl substituents together is at most 8.

2. A process as in claim 4 wherein R is formyl.

3. A process as in claim 4 wherein R is hydroxymethyl.

4. A process as in claim 4 wherein R is formoxymethyl.

5. A process as in claim 4 wherein R is acetoxymethyl.

6. A perfume composition containing as active perfuming ingredient an amount of a compound of the formula

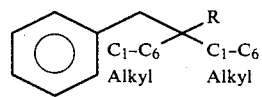

sufficient to impart a flowery odorous note thereto, wherein R is a formyl-, hydroxymethyl-, formoxymethyl-, acetoxymethyl- group and the total number of carbon atoms in both alkyl substituents together is at most 8.

7. A perfume composition as in claim 6 wherein R is formyl.

8. A perfume composition as in claim 6 wherein R is hydroxymethyl.

9. A perfume composition as in claim 6 wherein R is formoxymethyl.

10. A perfume composition as in claim 6 wherein R is acetoxymethyl.

11. A artificial essential oil of a flowery note resembling lily of the valley or hyacinth which comprises an amount of the formula

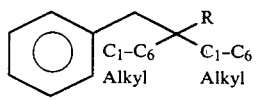

sufficient to impart the said flowery odorous note thereto, wherein R is a formyl-, hydroxymethyl-, formoxymethyl-, acetoxymethyl- group and the total number of carbon atoms in both alkyl substituents together is at most 8.

12. An artificial essential oil as in claim 11 wherein R is formyl.

13. An artificial essential oil as in claim 11 wherein R is hydroxymethyl.

14. An artificial essential oil as in claim 11 wherein R is formoxymethyl.

15. An artificial essential oil as in claim 11 wherein R is acetoxymethyl.

16. An artificial essential oil as in claim 11 which has the formula:

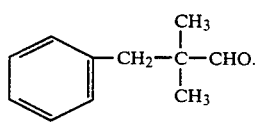

17. An artificial essential oil as in claim 11 which is of the formula:

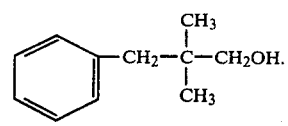

18. An artificial essential oil as in claim 11 which is of the formula:

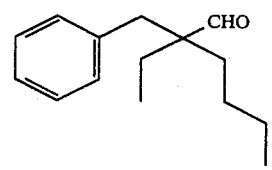

19. An artificial essential oil as in claim 11 which is of the formula:

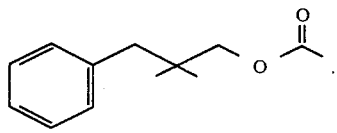

* * * * *